United States Patent
Bao et al.

(10) Patent No.: US 12,213,767 B2
(45) Date of Patent: Feb. 4, 2025

(54) VIDEO-BASED METHOD AND SYSTEM FOR ACCURATELY ESTIMATING HUMAN BODY HEART RATE AND FACIAL BLOOD VOLUME DISTRIBUTION

(71) Applicant: ZHEJIANG UNIVERSITY, Zhejiang (CN)

(72) Inventors: Hujun Bao, Hangzhou (CN); Xiaogang Xu, Hangzhou (CN); Xiaolong Wang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 412 days.

(21) Appl. No.: 17/696,909

(22) Filed: Mar. 17, 2022

(65) Prior Publication Data

US 2022/0218218 A1    Jul. 14, 2022

Related U.S. Application Data

(63) Continuation of application No. PCT/CN2021/080905, filed on Mar. 16, 2021.

(30) Foreign Application Priority Data

May 25, 2020  (CN) ......................... 202010448368.X

(51) Int. Cl.
*A61B 5/024*  (2006.01)
*A61B 5/00*   (2006.01)
(Continued)

(52) U.S. Cl.
CPC ........ *A61B 5/02416* (2013.01); *A61B 5/0295* (2013.01); *A61B 5/7232* (2013.01);
(Continued)

(58) Field of Classification Search
None
See application file for complete search history.

(56) References Cited

U.S. PATENT DOCUMENTS

| 7,756,577 B1 | 7/2010 | Kroll et al. |
| 2016/0287181 A1 | 10/2016 | Han et al. |

(Continued)

FOREIGN PATENT DOCUMENTS

| CN | 106845395 A | 6/2017 |
| CN | 107692997 A | 2/2018 |

(Continued)

OTHER PUBLICATIONS

Wen Yang et al "Heart Rate Estimation from Facial Videos Based on Convolutional Neural Network", IEEE 2018 (Year: 2018).*

(Continued)

*Primary Examiner* — Leon Flores
(74) *Attorney, Agent, or Firm* — W&G Law Group

(57) ABSTRACT

Provided is a video-based method and system for accurately estimating heart rate and facial blood volume distribution, and the method mainly comprises the following steps: firstly, carrying out face detection of video frame containing human face, and extracting face image sequence and face key position points sequence in time dimension; secondly, compressing these sequence of face image and face key position points to obtain the facial signals in time dimension; thirdly, estimating facial blood volume distribution by facial signals mentioned in third step; finally, estimating heart rate values by using model based on deep learning technology and the spectrum analysis method respectively, then fusing the estimation results by Kalman filter to promote the accuracy of heart rate estimation.

5 Claims, 4 Drawing Sheets

(51) Int. Cl.

| | |
|---|---|
| *A61B 5/0295* | (2006.01) |
| *G06T 7/00* | (2017.01) |
| *G06T 7/11* | (2017.01) |
| *G06T 7/73* | (2017.01) |
| *G06V 10/25* | (2022.01) |
| *G06V 10/62* | (2022.01) |
| *G06V 10/774* | (2022.01) |
| *G06V 10/80* | (2022.01) |
| *G06V 10/82* | (2022.01) |
| *G06V 40/16* | (2022.01) |
| *G16H 50/20* | (2018.01) |

(52) U.S. Cl.
CPC ............ *A61B 5/725* (2013.01); *A61B 5/7264* (2013.01); *G06T 7/0012* (2013.01); *G06T 7/11* (2017.01); *G06T 7/73* (2017.01); *G06V 10/25* (2022.01); *G06V 10/62* (2022.01); *G06V 10/774* (2022.01); *G06V 10/806* (2022.01); *G06V 10/82* (2022.01); *G06V 40/161* (2022.01); *G06V 40/171* (2022.01); *G16H 50/20* (2018.01); *G06T 2207/10016* (2013.01); *G06T 2207/20081* (2013.01); *G06T 2207/20084* (2013.01); *G06T 2207/30201* (2013.01); *G06V 2201/03* (2022.01)

(56) References Cited

U.S. PATENT DOCUMENTS

| | | | |
|---|---|---|---|
| 2017/0367590 | A1 | 12/2017 | Sebe et al. |
| 2021/0209388 | A1* | 7/2021 | Ciftci ................... G06V 10/764 |

FOREIGN PATENT DOCUMENTS

| | | |
|---|---|---|
| CN | 109460737 A | 3/2019 |
| CN | 109602412 A | 4/2019 |
| CN | 109700450 A | 5/2019 |
| CN | 110321781 A | 10/2019 |
| CN | 110458101 A | 11/2019 |
| CN | 111626182 A | 9/2020 |

OTHER PUBLICATIONS

International Search Report (PCT/CN2021/080905); Date of Mailing: Jun. 16, 2021.
CN First Office Action(202010448368.X); Date of Mailing: Dec. 15, 2020.
Notice Of Allowance(202010448368.X); Date of Mailing: Feb. 3, 2021.
ECG Heartbeat Classification Based on ResNet and Bi-LSTM; Date of Mailing: Jan. 17, 2020.

* cited by examiner

VIDEO-BASED METHOD AND SYSTEM FOR ACCURATELY ESTIMATING HUMAN BODY HEART RATE AND FACIAL BLOOD VOLUME DISTRIBUTION

CROSS-REFERENCE TO RELATED APPLICATIONS

The present application is a continuation of International Application No. PCT/CN2021/080905, filed on Mar. 16, 2021, which claims priority to Chinese Application No. 202010448368.x, filed on May 25, 2020, the contents of both of which are incorporated herein by reference in their entireties.

TECHNICAL FIELD

The present application relates to the accurate estimation of human heart rate and facial blood volume distribution by camera, based on image processing, deep learning and signal processing technologies.

BACKGROUND

Human heart rate and facial blood volume distribution are important indicators for human physiological health measurement. At present, the main ways to measure the human heart rate are ECG signal detection, photoelectric signal detection and other methods. The common characteristics of these methods is that the equipment for detection needs to cling to the skin of person being tested, to estimate heart rate from the skin potential activity. However, the limitation of this method is need to wear sensors, which limit the applicable scope of this kind of method. At present, remote detection of human physiological indicators through cameras has become a hot spot in current research. Because of the complexity of measurement environment of actual application scenarios, it is easy to cause interference to remote detection methods. In order to eliminate the interference mention above, signal decomposition methods such as wavelet decomposition, independent component analysis (ICA), principal component analysis (PCA) and Hilbert-Huang transform (HHT) are usually used alone or in combination to remove noises. The influence of noises cannot be eliminated well by a signal decomposition method, which is mainly due to the following two reasons: 1, a signal decomposition model is often a general decomposition algorithm, the prior information of physiological features of the human heart rate is not introduced; 2, the selection of decomposition results depends on subjective judgment, that is, the signal closest to heart rate features is selected from the decomposition results, which lacks an objective judgment standard. In order to improve the robustness and accuracy of the method of remote detection, the present application adopts deep learning technology, spectrum analysis and correlation calculation methods for detect the human heart rate and facial blood volume distribution, at the same time adopts Kalman filtering algorithm to fuse the results of heart rate by variety of ways, thus realizing accurate estimation of human heart rate.

SUMMARY

In order to improve the detection efficiency of the human heart rate and facial blood volume distribution, the present application provides a new detection method and system for human heart rate and facial blood volume distribution. Based on facial data of the video which used to analysis and processes for realizing the estimation of the human heart rate and facial blood volume distribution by means of model prediction and signal processing.

The present application is realized by the following technical solution: a video-based method for accurately estimating human heart rate and facial blood volume distribution, including the following steps:

(1) detecting and extracting human face image sequence and face key points sequence in time dimension from video; extracting global face signal and a set of face roi signals based on the face image sequence; preprocessing the signals;

(2) estimating heart rate value and facial blood volume distribution based on the set of the face roi signals which have been preprocessed;

(3) using a multimodal to estimate heart rate which based on LSTM and residual convolution neural network architecture;

(4) fusing results of heart rate value estimated by step (2) and step (3) based on the Kalman filtering, thus promote the accuracy of heart rate estimation.

The present application based on video-based system for accurately estimating heart rate and facial blood volume distribution, including:

an image detection module used for detecting the human face region in video frame image, and extracting a human face image and face key position points sequence in time dimension; extracting an global face signal and a set of roi signals based on the face image sequence;

a preprocessing module used for preprocessing the global face signal and roi signals for generating reference signal and roi signals respectively;

a frequency spectrum-based heart rate estimation module used for calculating reference signal and frequency spectrum of reference signal in the linear weighting manner based on the preprocessed roi signal set, thus estimating heart rate value according to the extremum of the frequency spectrum, and estimating the facial blood volume distribution based on the reference signal and the roi signals mentioned above;

a multimodal heart rate estimate model constructed based on LSTM and residual convolution neural network used for estimating heart rate based on heart rate distribution probability;

use the fusion model to refine the heart rate estimation, which based on frequency spectrum-based heart rate estimation module and the multimodal heart rate estimation model.

Compared with the prior art, the present application has the following advantages:

1) The robustness and accuracy of heart rate estimation are improved based on the fusion method, which improves the anti-interference ability and accuracy of heart rate estimation. Firstly, the heart rate is estimated based on the extremum value of the frequency spectrum transformed from reference signal, but this method has poor robustness in practical due to noise interference, E.g. human face movement or external illumination intensity change will have a great impact on the results. Therefore, a multimodal adopting deep learning technology is used to estimating the heart rate value. On this basis, the Kalman filtering method is used to integrate the results of heart rate which estimated by the two methods discussed above, thus improving the robustness and the accuracy of heart rate estimation.
2) The method proposed for estimating face blood volume distribution based on the heart rate value with high accuracy. It can be seen that the estimation of face blood volume distribution is highly consistent to prior knowledge.
3) Rapid heart rate estimation based on deep learning method. In the present application, heart rate estimation method based on multimodal deep learning technology and facial video data is proposed. The deep learning model based on LSTM and RCNN architecture is used to extract the features of the input data in a short time, so as to realize the rapid estimation of the human heart rate. At the same time, the anti-interference capability of the model is improved by adding bad samples, such as the addition of face shakes and brightness changes in the training sample set.

DESCRIPTION OF EMBODIMENTS

The present application will be further described in detail with reference to the attached drawings and specific embodiments.

Figure 1:
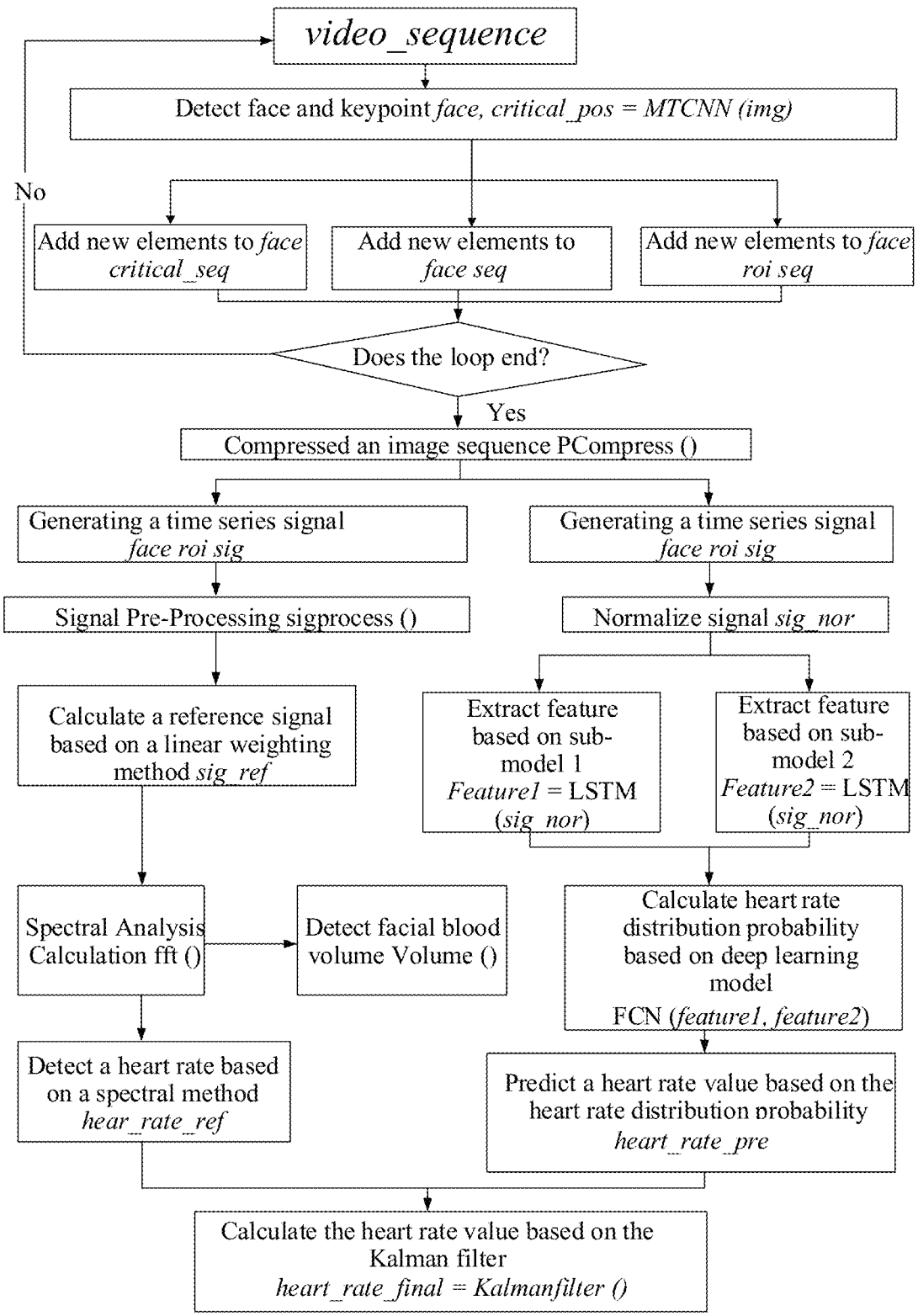
FIG. 1 is a flowchart of the method of the present application.

FIG. 1 is a schematic flow chart of the present application. In a specific embodiment of the present application, the present application is implemented by the following specific steps:
(1) Data extraction and preprocessing: a human face region in a video frame image is detected, then human face image sequence and face key position points sequence in time dimension are extracted; global face signal and the set of face roi signals are extracted based on the face image sequence; the signals mentioned above are preprocessed; the preprocessing method is not limited to band-pass filtering.
(1.1) A convolution network model is used to detect the face and face key points in video frames, then face image sequence and face key position point sequence in time dimension are respectively extracted, as shown in Formula 1, where MTCNN( ) is the convolution network model, $frame_i$ is the $i^{th}$ video frame image, $face_i$ is a face image extracted from the $i^{th}$ video frame, and $critical\_pos_i$ is the key position point of face image.

$$face_i, critical\_pos_i = MTCNN(frame_i) \quad (1)$$

The form of the face image sequence is shown in Formula 2, where: face_seq is the face image sequence, $face_i$ is the face image corresponding to the $i^{th}$ video frame, and T is the length of video.

$$face\_seq = \{face_1, face_2, \ldots, face_i, \ldots, face_T\} \quad (2)$$

(1.2) Based on face image sequence, the overall face signal and the set of face roi (region of interest) signals are extracted respectively. The calculation of the global face signal is shown in Formula 3, where: face_sig is a compressed signal, PCompress ( ) is a compression function, which used for calculating average pixel intensity of each image of the face image sequence, and face_seq is the face image sequence.

$$face\_sig = PCompress(face\_seq) \quad (3)$$

To facilitate the analysis of signal distribution, roi blocks with a size of R×R is used to segment face image in the sequence, then roi block sequences in time dimension are obtained, as shown in Formula 4, where: $face\_roi_i$ represents the $i^{th}$ roi block image sequence, and face_roi_seq is the set of roi block image sequences.

$$face\_roi\_seq = \{face\_roi_1, face\_roi_2, \ldots, face\_roi_i, \ldots, face\_roi_{m \times n}\} \quad (4)$$

On this basis, each roi block image sequence is compressed, as shown in Formula 5, where: face_roi_seq is a set of roi block image sequences, PCompress ( ) is the compression function for calculating the average pixel intensity of a image, and face_roi_sig is the result of PCompress( ) function.

$$face\_roi\_sig = PCompress(face\_roi\_seq) \quad (5)$$

where:

$$face\_roi\_sig = \{face\_roi\_sig_1, \ldots, face\_roi\_sig_i, \ldots, face\_roi\_sig_{m \times n}\} \quad (6)$$

In Formula 6, $face\_roi\_sig_i$ is the compressed signal corresponding to $i^{th}$ roi block, and m×n is the sum of face_roi_sig.
(1.3) Signal preprocessing: preprocess the global face signal and the face roi signal. The preprocessing method is not limited to band-pass filtering method, as shown in Formulas 7 and 8, where, face_sig_r and roi_sig_r are the results of sigprocess( ) correspond to face_sig and face_roi_sig, sigprocess( ) is the signal preprocessing function.

$$face\_sig\_r = sigprocess(face\_sig) \quad (7)$$

$$roi\_sig\_r = sigprocess(face\_roi\_sig) \quad (8)$$

where:

$$face\_sig\_r = \{face\_sig\_r_1, \ldots, face\_sig\_r_i, \ldots, face\_sig\_r_T\}$$

$$roi\_sig\_r = \{roi\_sig\_r_1, \ldots, roi\_sig\_r_i, \ldots, roi\_sig\_r_{m \times n}\}$$

where T is the length of video, m×n is the sum of roi_sig_r.
(2) Estimation of the heart rate and facial blood volume distribution. On the basis of the global face signal and the face roi signals calculated in step (1), the heart rate and facial blood volume distribution is estimated.
(2.1) A reference signal is calculated linearly, as shown in Formula 9, where sig_ref is the reference signal and roi_sig_r is the set of face roi signals as mentioned in Formula 8.

$$sig\_ref = weight\_set \times roi\_sig\_r = \sum_{i=1}^{m \times n} w_i \times roi\_sig\_r_i \quad (9)$$

$$weight\_set = \{w_1, w_2, \ldots, w_i, \ldots, w_{m \times n}\}$$

where: weight_set is a weight set and m×n is the sum of weight set.

(2.2) Based on the reference signal, the heart rate value is estimated. The estimation steps is shown in Formulas 11 and 12, where sig_ref is the reference signal, sig_ref_sd is the frequency spectrum of reference signal, and heart_rate_ref is the heart rate value corresponds to the peak of the sig_ref_sd. Signal spectrum calculation is not limited to the lomb-scargle spectrum analysis method.

$$\text{sig\_ref\_sd} = fft(\text{sig\_ref}) \tag{11}$$

$$\text{heart\_rate\_ref} = \max\_freq(\text{sig\_ref\_sd}) \tag{12}$$

(2.3) Estimation of facial blood volume distribution. In Formula 13, sig_ref_sd is the frequency spectrum of the reference signal, v is the blood volume distribution. the data feeded in Volume( ) function is not limited to the frequency spectrum of the reference signal.

$$v = \text{Volume}(\text{sig\_ref\_sd}) \tag{13}$$

In Formula 13, Volume( ) is the function for estimating blood volume distribution, and its specific form is shown in Formula 14.

$$\text{Volume}() = \begin{bmatrix} fs_{ref} \otimes fs_{roi}^{(1,1)} & fs_{ref} \otimes fs_{roi}^{(1,2)} & \cdots & fs_{ref} \otimes fs_{roi}^{(1,n)} \\ fs_{ref} \otimes fs_{roi}^{(2,1)} & fs_{ref} \otimes fs_{roi}^{(2,2)} & \cdots & fs_{ref} \otimes fs_{roi}^{(2,n)} \\ \vdots & \vdots & \ddots & \vdots \\ fs_{ref} \otimes fs_{roi}^{(m,1)} & fs_{ref} \otimes fs_{roi}^{(m,2)} & \cdots & fs_{ref} \otimes fs_{roi}^{(m,n)} \end{bmatrix} \tag{14}$$

In Formula 14, $fs_{ref}$ is the frequency spectrum of the reference signal, $fs_{roi}$ is the frequency spectrum of the face roi signals, ⊗ is convolution operator, and m and n are the maximum value of roi blocks in horizontal and vertical coordinates.

(3) The heart rate estimation multi-model is constructed based on deep learning method. Based on the face key position points sequence used for obtaining the image sequence including forehead and cheek area which used to make training samples, and the multi-modal heart rate estimation model is constructed based on a LSTM and a Residual Convolutional Neural Network.

(3.1) Extraction of training samples. The face key position points extracted in step (1.1) are used to form a key point sequence in time dimension, as shown in Formula 15, where: $critical\_pos_i$ is face key position points in the $i^{th}$ video frame, and $img_i$ is $i^{th}$ video frame.

$$face_i, critical\_pos_i = \text{MTCNN}(img_i) \tag{15}$$

The form of $critical\_pos_i$ is shown in formula 16, and k is the sum of face key position points, and i is i-th video frame.

$$critical\_pos_i = \{pos_1^i, pos_1^i, \ldots, pos_k^i\} \tag{16}$$

Figure 3:
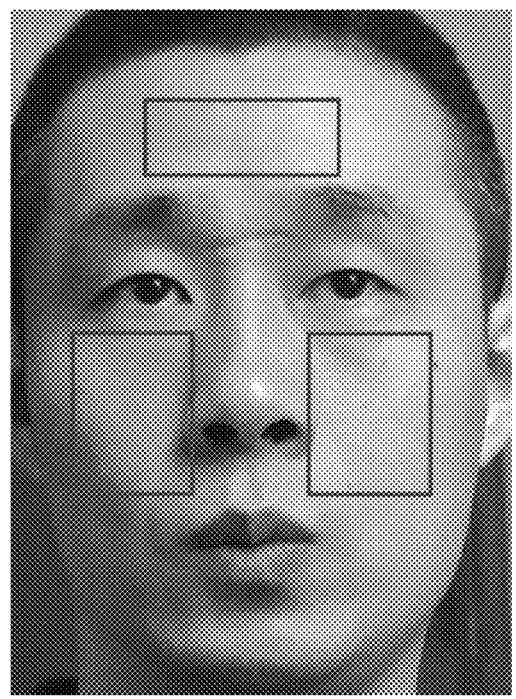
FIG. 3 is a schematic diagram of key areas of a face.

Based on the key position points of face, the image sequence consisting of forehead, left and right cheek regions in time dimension is selected as the critical roi showed in FIG. 3, then the selected image is compressed by PCcompress( ) function to construct training samples, as shown in Formula 17, where $sig\_c_i$ is the result of PCompress( ), $img\_c_i$ is the $i^{th}$ image of the critical roi sequence in time dimension, PCompress ( ) is the compression function.

$$\text{sig\_c}_i = \text{PCompress}(img\_c_i) \tag{17}$$

where:

$$\text{sig\_c} = \{\text{sig\_c}_1, \text{sig\_c}_2, \ldots, \text{sig\_c}_i, \ldots, \text{sig\_c}_T\}$$

In the above formula, sig_c is the result of compression of critical roi sequence, and T is video length.

(3.2) The training sample data is normalized, as shown in Formula 18, where sig_nor is the normalized signal, mean( ) is a mean calculation function, var( ) is a variance calculation function.

$$\text{sig\_nor} = \frac{\text{sig\_c} - \text{mean}(\text{sig\_c})}{\text{var}(\text{sig\_c})} \tag{18}$$

(3.3) A heart rate estimation module is constructed by LSTM (Long and Short Time Memory Network) architecture. This module constitutes by 1D-CNN (one dimension Convolutional Neural Network) and LSTM. First, sig_nor mention in Formula 18 feeds to 1D-CNN. On this basis, the LSTM is used to extract the time series features. Finally, attention mechanism is used to fuse the feature vector of various stages output of the LSTM, In Formula 19, LSTM( ) is the heart rate estimation module based on the LSTM and 1D-CNN mentioned above, sig_nor is the normalized signal obtained in step (3.2) and $feature_{lstm}$ is the result of LSTM( ) sub-model.

$$feature_{lstm} = \text{LSTM}(\text{sig\_nor}) \tag{19}$$

(3.4) A heart rate estimation sub-model is constructed based on the Resnet. The module is mainly constituted by the residual convolution neural network model to extract the features of the signal, the output feature vector of this module is shown in Formula 20, where Resnet( ) is the heart rate estimation module based on the Resnet architecture, sig_nor is the normalized signal obtained in step (3.2), $feature_{resnet}$ is the result of Resnet( ).

$$feature_{resnet} = \text{Resnet}(\text{sig\_nor}) \tag{20}$$

(3.5) The modules in step (3.3) and (3.4) are fused to construct a heart rate estimation multi-model. Result of the modules in step (3.3) and step (3.4) are connected to form the integrated feature vector, based on this, the heart rate can be estimated by fully connected network (FCN). The multi-model mentioned above is shown in Formula 21, where res_pro is the result vector from FCN( ), FCN( ) is the fully connected network, and Concat( ) is the vector connection function.

$$res\_pro = \text{FCN}(\text{Concat}(feature_{lstm}, feature_{resnet})) \tag{21}$$

On this basis, heart rate value is estimated as shown in Formula 22, where: heart_rate_pre is the heart rate value, mean( ) is the mean calculating function, and max_reg( ) is a function for searching for a heart rate range corresponding to the maximum probability.

$$\text{heart\_rate\_pre} = \text{mean}(\max\_reg(res\_pro)) \tag{22}$$

(4) Fusion of heart rate estimation results based on a Kalman filter. Based on the heart rate values estimated in steps (2) and (3), a signal quality evaluation value and a deep learning model estimation value are used as the state variables of the Kalman filter method, which are used to dynamically fuse the results of two heart rate estimating methods, thereby obtaining the best estimation of the heart rate value.

The Kalman filter model is shown in Formulas 23 and 24, where $x_k$ and $z_k$ are a predicted value and a measured value respectively, A and B are a state matrix and a control matrix respectively, H is transformation matrix from prediction space to measurement space, and $w_{k-1}$ and $v_k$ are a prediction error and a measurement error respectively.

$$x_k = Ax_{k-1} + Bu_k + w_{k-1} \tag{23}$$

$$z_k = Hx_k + v_k \tag{24}$$

According to Formulas 25 and 26, the heart rate values estimated by the two measurement methods mentioned in step (2) and (3) are fused, where $x_k$ is the predicted heart rate value estimated in step (3), $z_k$ is the heart rate value estimated in step (2), K is the fusion coefficient, H represents the transformation matrix from a prediction space to a measurement space, and H=1 in heart rate measurement. $P_k$ is a predicted variance, which corresponds to the predicted probability value in step (3). $R_k$ is a measured variance, which corresponds to the signal-to-noise ratio of the reference signal in step (2.3).

$$x'_k = x_k + K(z_k - Hx_k) \tag{25}$$

$$K = \frac{P_k H^T}{HP_k H^T + R_k} \tag{26}$$

The present application discloses a video-based system for accurately estimating human heart rate and facial blood volume distribution.

An image detection module is use for detecting human face region in the video frame and extract human face image sequence and key position points sequence of face in time dimension; extracting an global face signal and a set of face roi signals based on the face image sequence.

A preprocessing module preprocesses the global face signal and the roi signals extracted by the image detection module.

A frequency spectrum-based heart rate estimation module is used for estimating heart rate based on reference signal. Reference signal calculated in a linear weighting way based on the set of face roi signals, thus obtaining the heart rate value according to the extremum value of the frequency spectrum of reference signal, on this basis, the facial blood volume distribution can be calculated according to the frequency spectrum of the reference signal and the frequency spectrum of the roi signals.

A multimodal heart rate estimation model is constructed by LSTM and RCNN architecture which is used for estimating heart rate value based on heart rate distribution probability.

A fusion module is used for obtaining the fused heart rate value based on the results estimated by the frequency spectrum-based heart rate estimation module and the multimodal heart rate estimation model.

Figure 2:
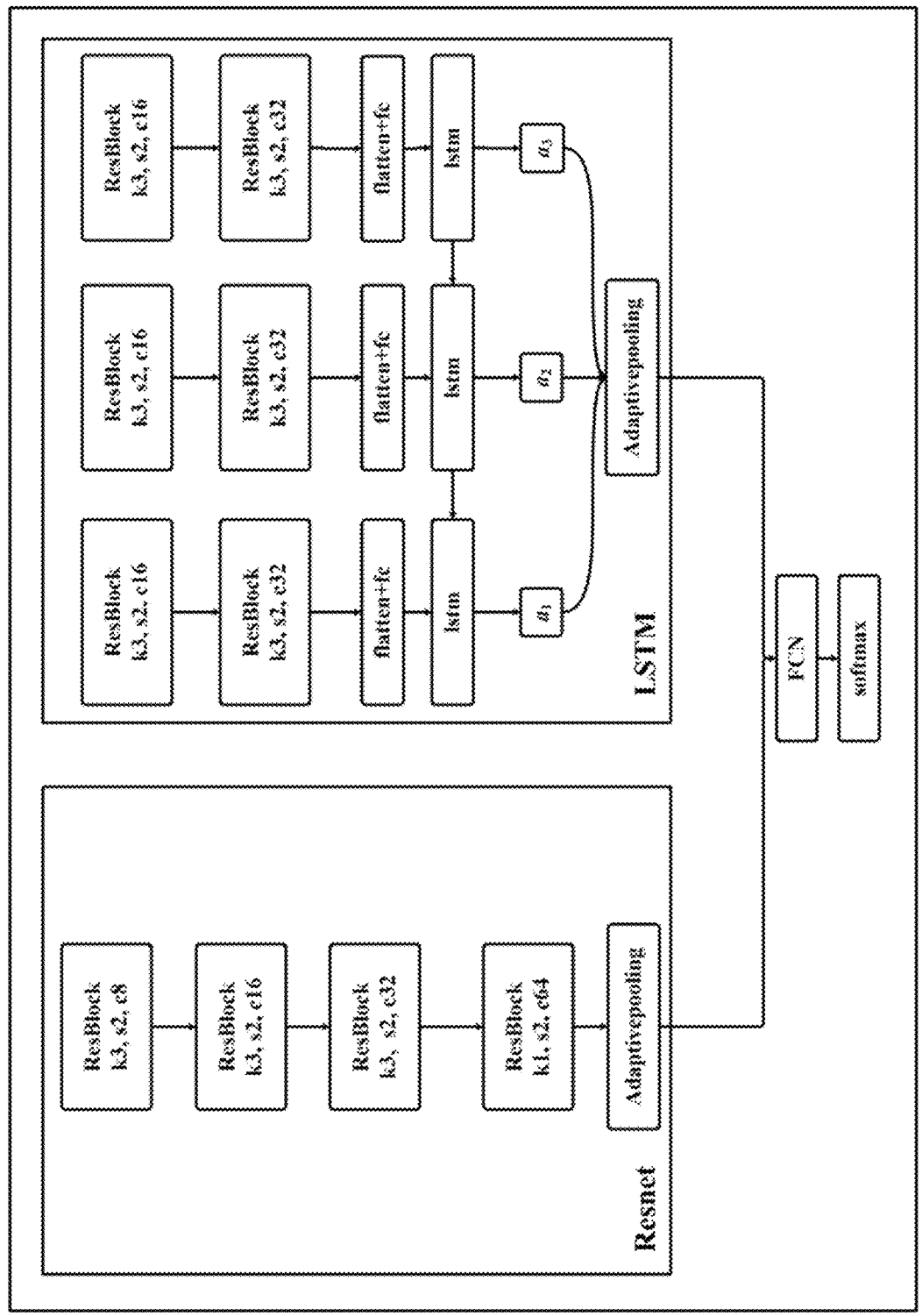
FIG. 2 is a structure diagram of the heart rate estimation model.

FIG. 2 is the structural diagram of multimodal heart rate estimation model according to the present application The left sub-picture (Resnet) of FIG. 2 is the CNN module, which is responsible for extracting the spatial features of data, and the right sub-picture (LSTM) is the LSTM module, which is used for extracting the features of the data in time dimension. The output feature vectors of the above two modules are combined to estimate the heart rate value.

FIG. 3 is a schematic diagram of key areas on a face; in the present application, the key areas on a face refer to the forehead and cheeks.

Figure 4:
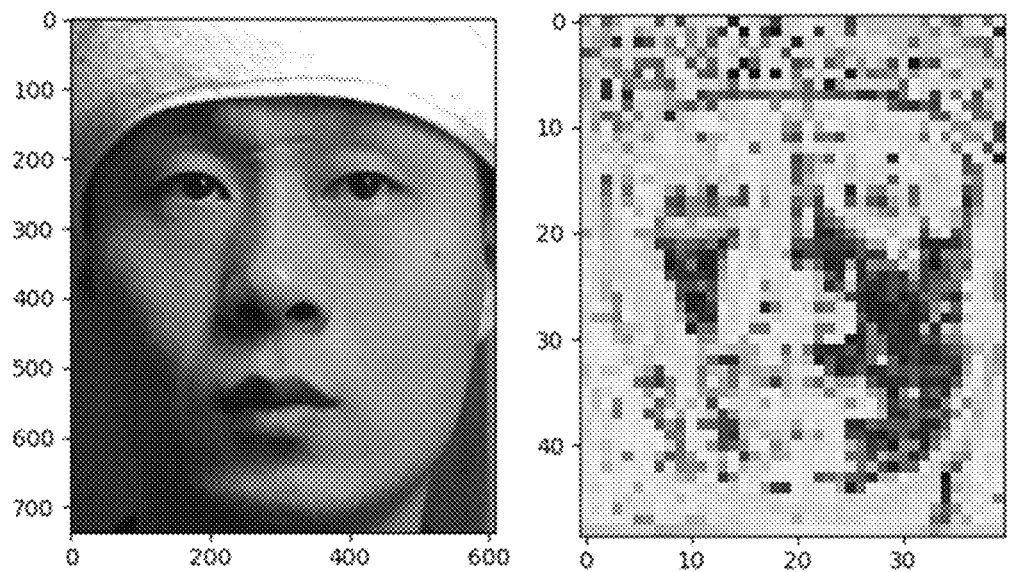
FIG. 4 shows results of a facial blood volume test 1.

FIG. 4 shows facial blood volume distribution results 1. The head is kept in a stable state. From the results, it can be seen that no blood volume distribution is detected on the forehead and the part with poor illumination, which is in line with the experimental expectation.

Figure 5:
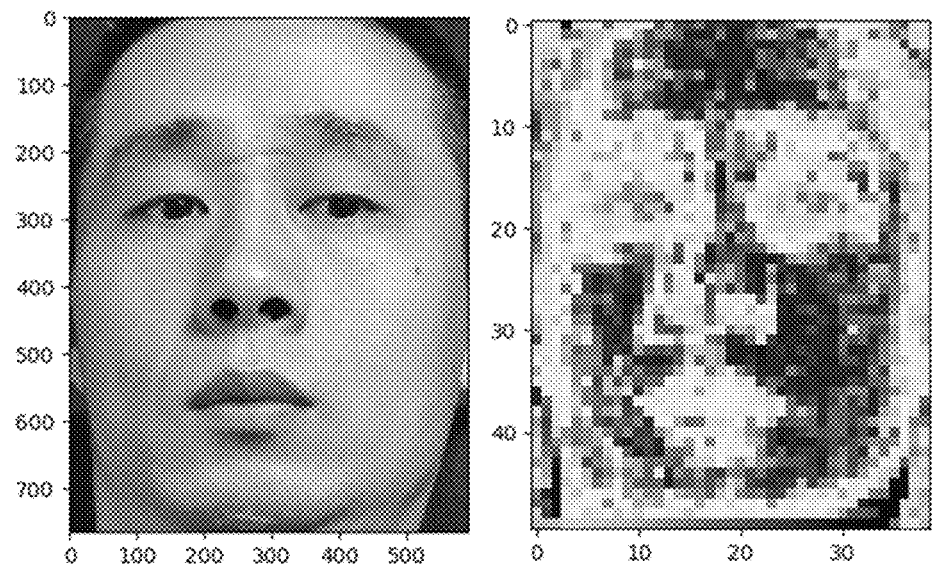
FIG. 5 shows results of a facial blood volume test 2.

FIG. 5 shows facial blood volume distribution results 2. The head is stabilized by a lying posture and the illumination is uniform. From the results, it can be seen that the results of the facial blood volume detection are uniform, which is in line with experimental expectation.

Figure 6:
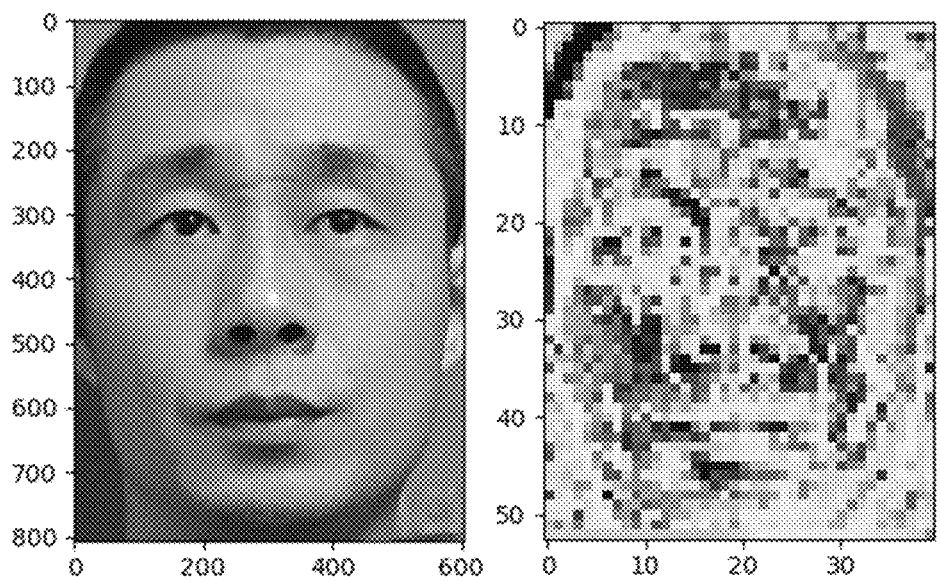
FIG. 6 shows results of a facial blood volume test 3.

FIG. 6 shows facial blood volume distribution results 3. The head is deliberately shaken slightly. Compared with the detection results shown in FIG. 5, it can be seen that the results of the facial blood volume detection have noises which is in line with experimental expectation.

The above embodiments are only the preferred embodiments of the present application, and it should be pointed out that for a person skilled in the technical field, several improvements and variations can be made without departing from the technical principle of the present application, and these improvements and variations should also be regarded as the protection scope of the present application.

What is claimed is:

1. A video-based method for accurately estimating a human heart rate and facial blood volume distribution, comprising the following steps:

(1) detecting a human face region in video frame, and extracting a human face image sequence and face key position points in time dimension, extracting a global face signal and a set of face roi signals based on the face image sequence, preprocessing the signals;

wherein the step (1) specifically comprises:

(1.1) using a convolution neural network model to detect the human face region and the face position key points in the video frame, and respectively generating a human face image sequence and a face key position point sequence in time dimension;

(1.2) extracting the global face signal and the set of the face roi signals, respectively, based on the face image sequence, the global face signal can be extracted as shown by Formula 3, where: face_sig is a compressed signal, PCompress ( ) is a compression function which is used to calculate an average pixel intensity of a face image of the face image sequence, and face_seq is the face image sequence;

$$\text{face\_sig} = \text{PCompress}(\text{face\_seq}) \tag{3}$$

segmenting the face image by roi blocks with R×R size to obtain roi block image sequences in time dimension, as shown in Formula 4, where: face_roi_$i$ represents an $i^{th}$ roi block image sequence, face_roi_seq is a set of roi block image sequences, and m×n is a sum of the roi blocks;

$$\text{face\_roi\_seq} = \{\text{face\_roi}_1, \text{face\_roi}_2, \ldots, \text{face\_roi}_i, \ldots, \text{face\_roi}_{m \times n}\} \tag{4}$$

compressing each roi block image sequence, as shown in Formula5, where: face_roi_seq is the set of roi block image sequences, PCompress ( ) is the compression function for calculating mean of pixel intensity of the image of the sequence, and face_roi_sig is the result of PCompress ( );

$$face\_roi\_sig = PCompress(face\_roi\_seq) \quad (5)$$

where:

$$face\_roi\_sig = \{face\_roi\_sig_1, \ldots, face\_roi\_sig_i, \ldots, face\_roi\_sig_{m \times n}\} \quad (6)$$

in Formula 6, face_roi_sig$_i$ is a signal compressed by the i$^{th}$ roi block image sequence, and m×n is the sum of the roi blocks;

(1.3) preprocessing the global face signal and the set of the face roi signals to eliminate components outside a specified frequency range;

(2) estimate heart rate value and facial blood volume distribution based on a reference signal and the set of roi signals;

(3) estimate heart rate value based on heart rate distribution probability by using a heart rate estimation model based on Long and Short Time Memory Network (LSTM) and a residual convolution neural network model;

(4) fusing results of the heart rate value of the step (2) and the step (3) based on Kalman filtering.

2. The video-based method for accurately estimating a human heart rate and a facial blood volume distribution according to claim 1, wherein the step (2) specifically comprises:

(2.1) calculating the reference signal by linear weighting, as shown in Formula 9, where sig_ref is the reference signal, roi_sig_r is the preprocessed set of the face roi signals, and m×n is the sum of the roi blocks;

$$sig\_ref = weight\_set \times roi\_sig\_r = \sum_{i=1}^{m \times n} w_i \times roi\_sig\_r_i \quad (9)$$

$$weight\_set = \{w_1, w_2, \ldots, w_i, \ldots, w_{m \times n}\}$$

$$roi\_sig\_r = sig \text{ process}(face\_roi\_sig) \quad (8)$$

where: weight_set is a calculated weight set; sigprocess ( ) is a signal preprocessing function;

(2.2) calculating a frequency spectrum of the reference signal by using a lomb-scargle spectrum analysis method, the heart rate value corresponds to a extremum value of the frequency spectrum;

(2.3) estimating the facial blood volume distribution.

3. The video-based method for accurately estimating human heart rate and a facial blood volume distribution according to claim 2, wherein the step (2.3) is specifically as below:

as shown in Formula 13, sig_ref_sd is the spectrum of the reference signal, and v is the blood volume distribution;

$$v = Volume(sig\_ref\_sd) \quad (13)$$

where, Volume ( ) is a function for calculating the blood volume distribution, a specific form of which is shown in Formula 14;

$$Volume() = \begin{bmatrix} fs_{ref} \otimes fs_{roi}^{(1,1)} & fs_{ref} \otimes fs_{roi}^{(1,2)} & \ldots & fs_{ref} \otimes fs_{roi}^{(1,n)} \\ fs_{ref} \otimes fs_{roi}^{(2,1)} & fs_{ref} \otimes fs_{roi}^{(2,2)} & \ldots & fs_{ref} \otimes fs_{roi}^{(2,n)} \\ \vdots & \vdots & \ddots & \vdots \\ fs_{ref} \otimes fs_{roi}^{(m,1)} & fs_{ref} \otimes fs_{roi}^{(m,2)} & \ldots & fs_{ref} \otimes fs_{roi}^{(m,n)} \end{bmatrix} \quad (14)$$

in Formula 14, fs$_{ref}$ is a frequency spectrum of the reference signal, fs$_{roi}$ is a frequency spectrum of the roi signal, $\otimes$ is a convolution operator, and m and n are sum of the roi blocks in horizontal and vertical directions, respectively.

4. The video-based method for accurately estimating human heart rate and facial blood volume distribution according to claim 1, wherein in step (3), a training method of the heart rate estimation model constructed based on the LSTM and the residual convolution neural network model is as follows:

(3.1) making training samples forming a key point sequence in time dimension based on the face key position points extracted in step (1), selecting an image sequence formed by forehead, left and right cheek regions in time dimension based on the face key position points, and compressing the selected critical images to construct training samples;

(3.2) normalizing train samples to obtain the normalized train samples sig_nor;

(3.3) constructing a heart rate estimation module based on the LSTM;

wherein the module includes two network structures of One-dimension Convolutional Neural Network (1D-CNN) and LSTM; firstly, the sig_nor signal obtained in step (3.2) is used as the input data of this module, and preliminary features corresponding to the sig_nor signal are extracted based on the 1D-CNN sub-module, on this basis, LSTM sub-module is used to extract features; finally, fusing feature vectors of various stage output of the LSTM by using an attention mechanism, then obtain the highest level feature vector expressed as feature$_{lstm}$;

(3.4) constructing the heart rate estimation module based on Resnet;

wherein the module extracts features of waveform distribution of the signal based on Resnet, and takes the sig_nor as an input sample of the module, then obtain the highest level feature vector expressed as feature$_{resnet}$;

(3.5) fusing the modules in steps (3.3) and (3.4) to construct the heart rate estimation multi-model;

combine output features of the modules in step (3.3) and step (3.4) into feature vector, then estimate heart rate value by the fully connected network (FCN);

wherein a basic estimation process is shown in Formula 21, where: res_pro is a model estimation result vector, FCN ( ) is a fully connected layer, and Concat ( ) is a vector combining function;

$$res\_pro = FCN(Concat(feature_{lstm}, feature_{resnet})) \quad (21)$$

on this basis, the heart rate value is estimated, and a basic process of extracting the heart rate value is shown in Formula 22, where: heart_rate_pre is a heart rate estimation value, mean ( ) is a mean function, and max_reg ( ) is a function for searching for a heart rate range corresponding to a maximum probability value;

$$\text{heart\_rate\_pre} = \text{mean}(\text{max\_reg}(\text{res\_pro})) \qquad (22)$$

5. The video-based method for accurately estimating human heart rate and facial blood volume distribution according to claim 1, wherein the step (4) specifically comprises:

fusing the heart rate values obtained by two estimating methods shown in Formulas 25 and 26, $$x'_k = x_k + K(z_k - Hx_k) \qquad (25)$$

$$K = \frac{P_k H^T}{H P_k H^T + R_k} \qquad (26)$$

where $x_k'$ is a fused heart rate value, $x_k$ is the heart rate estimation value obtained in step (3), $z_k$ is the heart rate value obtained in step (2), K is a fusion coefficient, $P_k$ is a predicted variance, $R_k$ is a measured variance, and H and $H^T$ represents a relation matrix and a transposition form thereof, respectively.

\* \* \* \* \*